(12) United States Patent
Huang et al.

(10) Patent No.: US 11,026,571 B2
(45) Date of Patent: Jun. 8, 2021

(54) METHOD FOR PROCESSING PUPIL TRACKING IMAGE

(71) Applicant: WENZHOU MEDICAL UNIVERSITY, Wenzhou (CN)

(72) Inventors: Jinhai Huang, Wenzhou (CN); Hang Yu, Wenzhou (CN); Meixiao Shen, Wenzhou (CN); Hao Chen, Wenzhou (CN)

(73) Assignee: WENZHOU MEDICAL UNIVERSITY, Wenzhou (CN)

( * ) Notice: Subject to any disclaimer, the term of this patent is extended or adjusted under 35 U.S.C. 154(b) by 153 days.

(21) Appl. No.: 16/469,587

(22) PCT Filed: Dec. 13, 2018

(86) PCT No.: PCT/CN2018/120832
§ 371 (c)(1),
(2) Date: Jun. 13, 2019

(87) PCT Pub. No.: WO2020/098038
PCT Pub. Date: May 22, 2020

(65) Prior Publication Data
US 2020/0305705 A1    Oct. 1, 2020

(30) Foreign Application Priority Data
Nov. 12, 2018    (CN) .......................... 201811337008.1

(51) Int. Cl.
*G06K 9/00*    (2006.01)
*A61B 3/10*    (2006.01)
(Continued)

(52) U.S. Cl.
CPC .......... *A61B 3/0025* (2013.01); *A61B 3/0008* (2013.01); *A61B 3/112* (2013.01);
(Continued)

(58) Field of Classification Search
CPC .......... A61B 3/103; A61B 3/14; A61B 3/113; A61B 3/1225; A61B 3/024; A61B 3/032;
(Continued)

(56) References Cited

U.S. PATENT DOCUMENTS 5,481,622 A * 1/1996 Gerhardt ................ A61B 3/113
345/158
6,299,307 B1    10/2001 Oltean et al.
(Continued)

FOREIGN PATENT DOCUMENTS

CN    104268527 A    1/2015
CN    104463159 A    3/2015
(Continued)

*Primary Examiner* — Dawayne Pinkney
(74) *Attorney, Agent, or Firm* — Christensen, Fonder, Dardi & Herbert PLLC

(57) ABSTRACT

A method for processing pupil tracking images, comprising the steps of: 1) acquiring eye images multiple times; 2) processing each acquired eye image, and determining whether a pupil can be positioned in the acquired image; and 3) determining that pupil tracking is completed when the pupil can be positioned in consecutive n pieces of eye images. Image processing efficiency is improved by searching a potential bright spot area and carrying out Blob analysis smearing images caused by pupil movement can be eliminated, the pupil edge is accurately positioned by adopting a line drawing method in collaboration with a support vector machine when determining the pupil edge, and finally a weighted least square method is adopted to fit a circle/ellipse (pupil). Therefore, real-time tracking and analysis of the pupil under a complex background are realized, and reliable data are provided for subsequent steps to obtain the refractive parameters of the eye.

8 Claims, 4 Drawing Sheets

(51) Int. Cl.
*A61B 3/14* (2006.01)
*A61B 3/00* (2006.01)
*A61B 3/11* (2006.01)
*G06T 7/00* (2017.01)
*G06T 7/60* (2017.01)

(52) U.S. Cl.
CPC .............. *G06T 7/0012* (2013.01); *G06T 7/60* (2013.01); *G06T 2207/30041* (2013.01)

(58) Field of Classification Search
CPC ........ A61B 3/02; A61B 3/18; G06K 9/00597; G06K 9/00158; G06K 9/00228; G07C 9/00158; G02C 3/005
USPC ................ 351/200, 204–210, 221–223, 240, 351/243–246
See application file for complete search history.

(56) References Cited

U.S. PATENT DOCUMENTS

| | | | | |
|---|---|---|---|---|
| 2004/0005083 A1* | 1/2004 | Fujimura | ............... | A61B 3/113 382/103 |
| 2004/0196433 A1* | 10/2004 | Durnell | .............. | G06K 9/00604 351/209 |
| 2010/0284576 A1 | 11/2010 | Tosa | | |

FOREIGN PATENT DOCUMENTS

| | | |
|---|---|---|
| CN | 105488487 A | 4/2016 |
| CN | 105590109 A | 5/2016 |
| CN | 105678286 A | 6/2016 |
| CN | 106203358 A | 12/2016 |

\* cited by examiner

METHOD FOR PROCESSING PUPIL TRACKING IMAGE

RELATED APPLICATIONS

The present application is a National Phase entry of PCT Application No. PCT/CN2018/120832, filed Dec. 13, 2018, which claims priority to Chinese Patent Application No. 201811337008.1, filed Nov. 12, 2018, the disclosures of which are hereby incorporated by reference herein in their entirety.

TECHNICAL FIELD

The invention relates to an ophthalmology image processing method, in particular to a method for processing pupil tracking images.

BACKGROUND ART

Retinoscopy optometry is the golden standard for examination of ametropia, and the accuracy can reach 0.25 D. But for children, the retinoscopy optometry has the limitation in its application. A hand-held vision screening instrument is a special instrument designed and produced in recent years for infant vision examination, characterized in that the examination can be carried out under the condition of keeping a certain distance with the subject, and the subject has not to show high coordination. The method is not only suitable for people with good coordination, but also suitable for vision screening of infants and people with poor coordination, as compared with the conventional examination method.

The instrument uses infrared light source for projecting to the retina, light reflected by the retina presents different patterns under different refraction states, and a camera records the patterns and obtains data such as a spherical lens, a cylindrical lens and an axial position through calculation. The instrument may obtain the refraction state, the pupil diameter, the pupil distance, the eye position and other information of both eyes from measurement for once, so that a doctor can quickly screen and have a comprehensive understanding of the vision development state of a patient.

According to the principle of eccentric photography optometry, a light source array is formed by a near-infrared light-emitting diode, rays of light are emitted to an examined pupil from a certain distance at a specific angle to enter the retina and are reflected by the retina, and during the period, the light rays are emitted from the pupil area after being refracted twice by an eyeball refraction system (refracted when both entering and exiting eyes) and are shot by a camera. The refractive and accommodative states of the eye to be examined thus determine the shape and brightness of the shadow in the pupil area of the eye to be examined. And the pupil shadow image is processed and analyzed to obtain a corresponding vision examination result.

SUMMARY OF THE INVENTION

Directed to the above, the invention provides a method for processing pupil tracking images.

To achieve the above object, the invention provides a method for processing pupil tracking images, including the steps of:
1) acquiring eye images for multiple times;
2) processing each acquired eye image, and determining whether a pupil can be positioned in the acquired image; and
3) determining that the pupil tracking is completed when the pupil can be positioned in consecutive n pieces of eye images.

In step 2), the processing method for each acquired eye image includes the steps of:
step 1, searching bright spots formed by projection of illumination light on a pupil;
step 2, performing Blob analysis on the bright spots to determine a potential pupil area;
step 3, carrying out gray normalization on the potential pupil area and carrying out multi-scale binarization;
step 4, finding a potential circular area through Blob analysis, and obtaining a gravity center and a rough radius of the circular area;
step 5, taking the gravity center obtained in step 4 as the center of a circle, adopting a 360-degree outward line drawing method to obtain gray level jump, and obtaining the maximum gray level jump of the left, right and lower parts of the pupil, namely the maximum jump being the boundaries of the left, right and lower parts of the pupil;
step 6, obtaining a boundary and determining the reliability of the boundary by adopting a support vector machine (SVM) according to a gray value obtained by a line drawing method, the boundary being an upper edge area of the pupil; and
step 7, according to the boundaries of the left, right, lower and upper parts of the pupil obtained in step 5 and step 6, the pupil is obtained by using a least square method to fit a circle.

In step 5, the relationship between the gray level on each drawn line and the distance is obtained.

In step 2, a pupil image obtained by eccentric photography optometry is examined, and whether the pupil moves or not is determined by judging the shape of the light spot.

In step 3, a multi-scale binarization threshold value is determined according to the gray mean value, the gray standard deviation, the gray minimum value and the gray maximum value of the pupil image, wherein the binarization threshold value=gray mean value$-\alpha$*gray standard deviation, and the coefficient $\alpha$ is an empirical value.

In step 6, a boundary is obtained by using a support vector machine (SVM) through the gray value sequence obtained by the 360-degree outward line drawing method in step 5.

In step 5, the maximum jump of the gray level is obtained through a difference method.

In step 7, a parameter equation of the circle is established as follows:

$$x = z_1 + r \cos \varphi$$

$$y = z_2 + r \sin \varphi$$

wherein $(z_1, z_2)$ is the coordinate of the circle center, r is a radius of the circle, $\varphi$ is a parameter, and each point on the circle is $T_i = (x(\varphi_i), y(\varphi_i))$, for an image pixel coordinate $P_i = (x_{i1}, x_{i2})$ required to be fitted with the circle, a least square method is used to fit distances form all the points $P_i$ to points $T_i$, and minimization is carried out, $$d_i^2 = \min[(x_{i1} - x(\varphi_i))^2 + (x_{i2} - y(\varphi_i))^2],$$

$$\sum_{i=1}^{m} d_i^2 = \min,$$

further, in order to obtain the contribution of different pixel coordinates to the circle fitting, the minimization may be made as $$\sum_{i=1}^{m} w_i * d_i^2 = \min,$$

$w_i$ is a weight coefficient.

The invention has the following advantages: according to the invention, the image processing efficiency is greatly improved by searching a potential bright spot area and carrying out Blob analysis, the smearing image caused by pupil movement can be eliminated, then the pupil edge is accurately positioned by adopting a line drawing method in collaboration with a support vector machine (SVM) when determining the pupil edge, and finally a weighted least square method is adopted to fit a circle/ellipse (pupil). Therefore, real-time tracking and analysis of the pupil under a complex background are realized, and reliable basic data are provided for subsequent steps to obtain the refractive parameters of the eye.

DETAILED DESCRIPTION OF THE INVENTION

Embodiments of the present invention are further described below with reference to the accompanying drawings.

Figure 1:
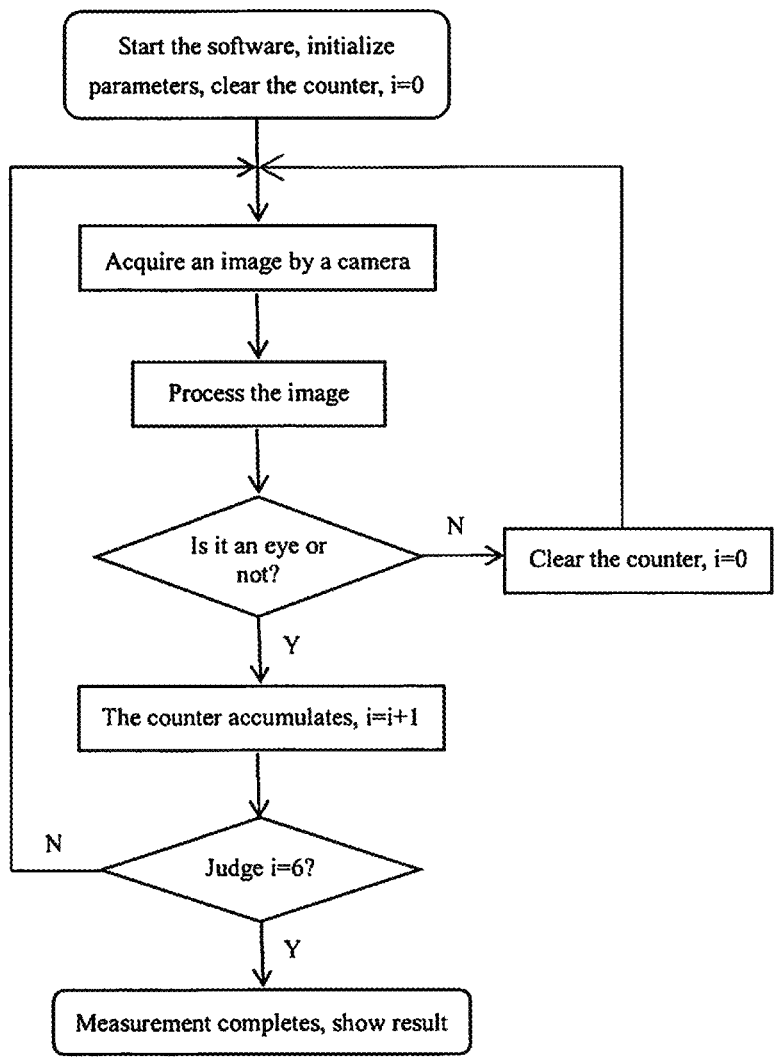
FIG. 1 is a schematic flow diagram of the present invention.
Figure 2:
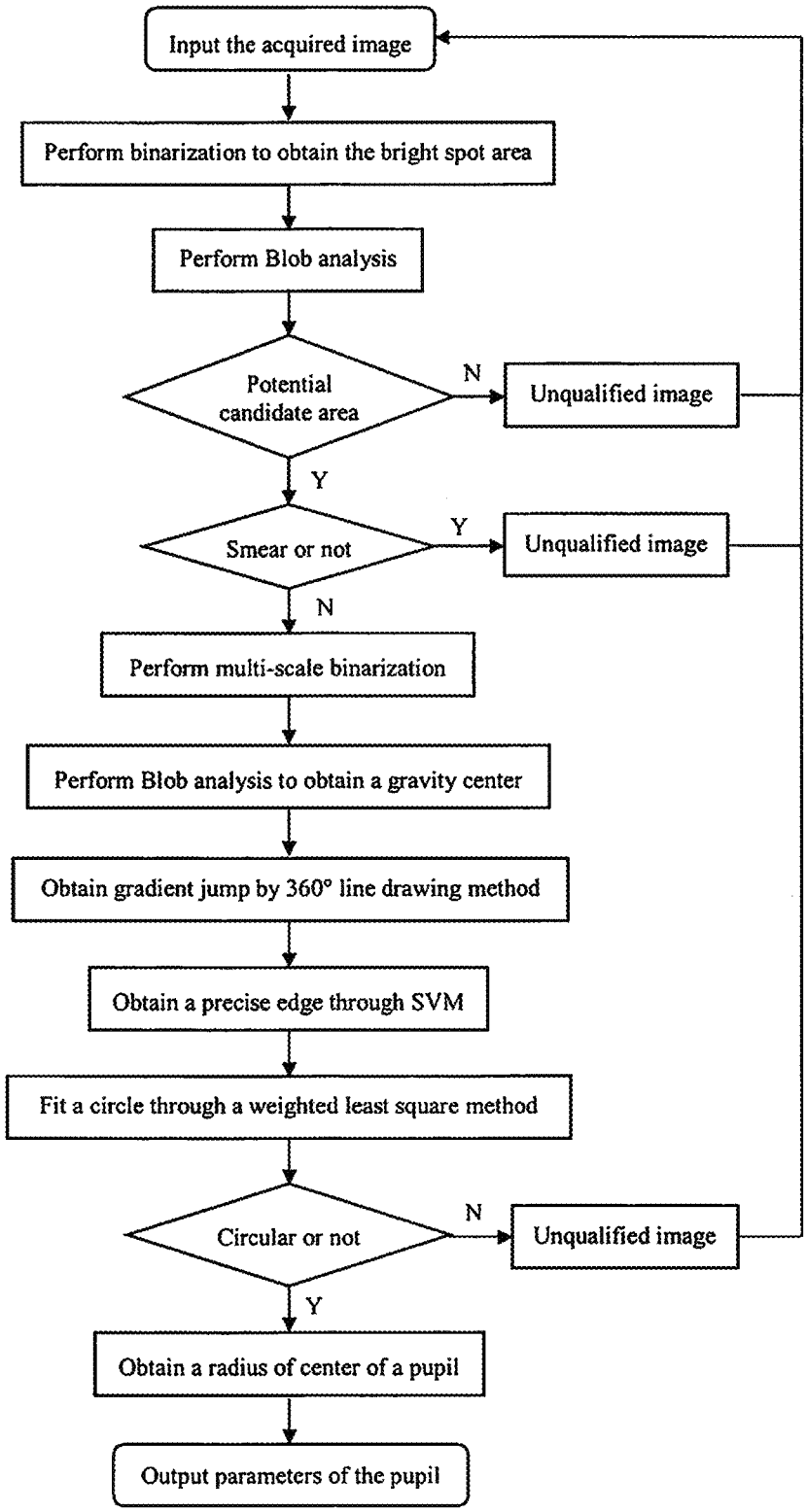
FIG. 2 is a flow chart of a single frame image processing algorithm of the present invention.

As shown in FIG. 1, the invention relates to an eccentric photography optometry image processing method based on machine vision, including the steps of: continuously acquiring eye images by a camera, carrying out processing of each image respectively, and completing tracking measurement if pupils can be positioned in six consecutive images successfully. The process of the method is as follows:

the system is first initialized and the counter is cleared, i.e., set to be i=0. An image is acquired by a camera, and the image is stored in a file format with a lower compression rate, such as a bmp or jpeg format, so as to ensure that the image has more local details;

in the steps that follow, the image acquired by the camera is processed, and in the single-frame image processing process, two common situations may cause inaccurate pupil tracking, one the occlusion of eyelashes, and the other image smears caused by the movement of the pupil, as a result the edge of the pupil cannot be accurately tracked, and the subsequent obtaining of gray level change in the interior of the pupil turns out to inaccurate, and finally the eye diopter is calculated to be incorrect. Accurate tracking of the edge of the pupil is therefore a guarantee of the accuracy of the eccentric photorefractive device.

Figure 3:
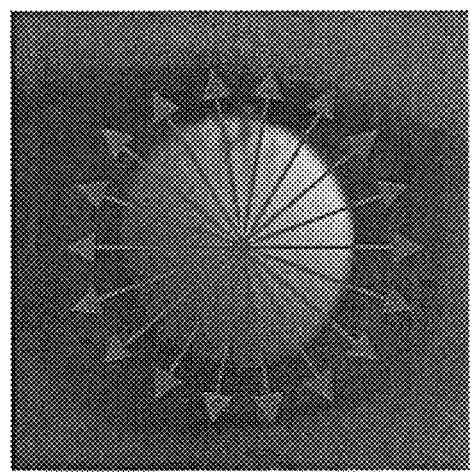
FIG. 3 is a schematic view of the line drawing method of the present invention.
Figure 4:
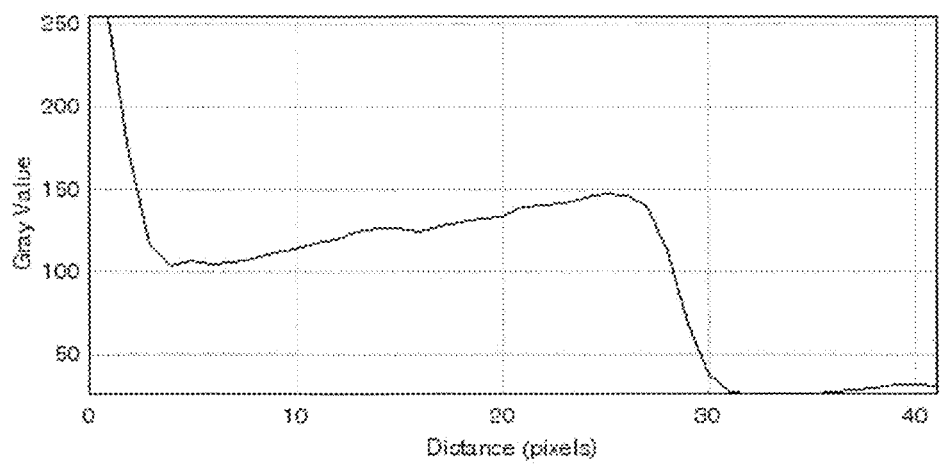
FIG. 4 is a gray level map on the drawn line.
Figure 5A:
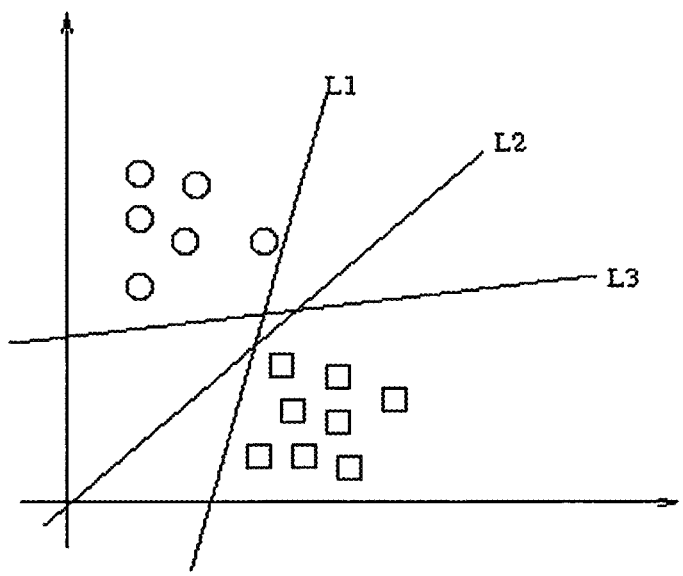
FIGS. 5a and 5b are schematic diagrams comparing a generic classifier with the SVM method.
Figure 5B:
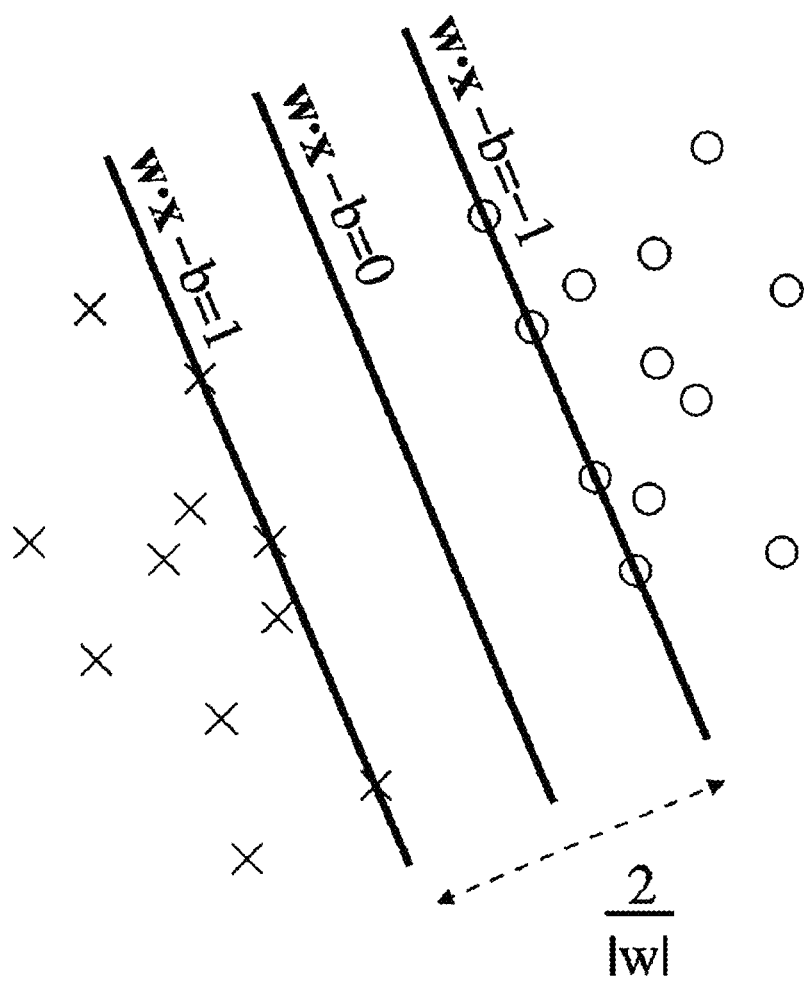

Therefore, the image is processed through the steps of:

step 1, searching a bright spot formed by projection of illumination light on a pupil, and trying to obtain a potential pupil area;

step 2, performing Blob analysis on the bright spots to determine a potential pupil area; wherein a pupil image obtained by eccentric photography optometry is examined, and whether the pupil moves or not is determined by judging the shape of the light spot;

where the smearing phenomenon is caused by the relative motion between the imaging system and the target pupil during the exposure time, which is also called motion blur; for blurred images, it is visible that the gray level of blurred areas changes relatively slowly, with smooth edges and thus the sharpness is less than that of clear areas; the commonly used methods for determining image blurs include using the fitting standard deviation and gradient amplitude of the gradient distribution of the image edge as the blur degree to determine the blur degree of the edge, calculating the frequency domain logarithm correlation coefficient of the pixel to determine whether the pixel is in a blurred area, or using the local standard deviation of the image to determine whether the image is blurred or not; however, excessive or missing detection often occurs on the blurred image generated by eccentric photography optometry, because the main purpose of the image is to extract the pupil edge, while the gray value of the pupil edge in some directions is relatively low and the gray difference between the pupil edge and the iris is small due to the eccentric photography, it is inherently difficult to extract the pupil edge, not to mention to determine whether the image is blurred or not; the brightest portion in the pupil image obtained by eccentric photography optometry is a bright spot formed by projecting an illumination light source on the pupil, when the pupil does not move, the spot is a small bright round point, when the pupil moves rapidly, the spot generates a smearing phenomenon, and the round point becomes a straight line or even an arc line, so that whether the pupil moves or not can be determined by detecting the shape features of the bright spot;

step 3, carrying out gray normalization on the potential pupil area and carrying out multi-scale binarization; wherein a multi-scale binarization threshold value is determined according to the gray mean value, the gray standard deviation, the gray minimum value and the gray maximum value of the pupil image, with the binarization threshold value=gray mean value−α*gray standard deviation, and the coefficient α being an empirical value;

where since the ambient light, the shooting distance, the angle, the position and the like of each shooting vary, the change of the image gray level is generated, and the photography optometry determines the diopter value according to the gray level change in the pupil, so that the gray level normalization is necessary, and the gray level error caused by external conditions is eliminated as much as possible; the multi-scale binarization threshold value is determined according to the gray mean value, the gray standard deviation, the gray minimum value and the gray maximum value of the pupil image, for example: binarization threshold value=gray mean value−α*gray standard deviation, where coefficient α is an empirical value, the binarization threshold value is determined by changing the value of α, and some boundary conditions can be added according to gray standard deviation, gray maximum and minimum values to ensure that the binarization threshold value does not cross the boundary or limit (α*gray level standard deviation);

step 4, finding a potential circular area through Blob analysis, and obtaining a gravity center and a rough radius of the circular area;

step 5, taking the gravity center obtained in step 4 as the center of a circle, adopting a 360-degree outward line drawing method to obtain gray level jump, and obtaining the maximum gray level jump of the left, right and lower parts of the pupil, namely the maximum jump being the boundaries of the left, right and lower parts of the pupil;

where the center of the circle is taken as a starting point, from which a line is drawn outward as shown in FIG. 3, the gray value on the image corresponding to the line is shown in FIG. 4, the horizontal axis represents the pixel distance from the starting point, and the vertical axis represents the gray value corresponding to the pixel value; for example, 18 lines are drawn at intervals of an angle of 20 degrees, a smaller degree interval indicates a higher sampling accuracy and also represents an increase in processing time; and the gray level jump on the drawn line can be obtained through a difference method;

step 6, obtaining a boundary and determining the reliability of the boundary by adopting a support vector machine (SVM) according to a gray value obtained by a line drawing method, the boundary being an upper edge area of the pupil;

where a support vector machine (SVM) is a method of supervised learning, widely used in statistical classification and regression analysis; SVM belongs to generalized linear classifiers which are characterized by their ability to simultaneously minimize empirical errors and maximize geometric edge areas; SVM is therefore also referred to as maximum edge area classifiers;

and the principal idea of SVM can be summarized as two aspects: (1) the method is used for analyzing the linear separable situation, and for the linear inseparable situation, a nonlinear mapping algorithm is used for converting a low-dimensional input space linearly inseparable sample into a high-dimensional feature space which is rendered to be linearly separable, so that the high-dimensional feature space can perform linear analysis on the nonlinear characteristic of the sample by adopting a linear algorithm; (2) based on the theory of structural risk minimization, the method constructs an optimal segmentation hyperplane in the feature space, so that the learner is globally optimized, and the expected risk in the whole sample space meets a certain upper bound with a certain probability;

and SVM maps vectors into a space of higher-dimension, where a maximum margin hyperplane is established; two hyperplanes parallel to each other are created on both sides of the hyperplane separating the data; the parallel hyperplanes are separated to maximize the distance therebetween; it is assumed that the larger the distance or gap between parallel hyperplanes is, the smaller the overall error of the classifier will be; there are many classifiers (hyperplanes) that can separate the data, but only one can achieve maximum segmentation; as shown in FIG. 5a, there are two types of objects, circular and square, which can be separated by lines L1, L2 and L3, and this is a common classification method; in FIG. 5b, the SVM classifier is used to segment the circular and x-shaped objects by using two parallel lines so as to maximize the separation between the two parallel lines and minimize the classification error; and step 7, according to the boundaries of the left, right, lower and upper parts of the pupil obtained in step 5 and step 6, the pupil is obtained by using a least square method to fit a circle;

where a parameter equation of the circle is established as follows:

$$x = z_1 + r \cos \varphi$$

$$y = z_2 + r \sin \varphi$$

wherein $(z_1, z_2)$ is the coordinate of the circle center, r is a radius of the circle, $\varphi$ is a parameter, and each point on the circle is $T_i = (x(\varphi_i), y(\varphi_i))$, for an image pixel coordinate $P_i = (x_{i1}, x_{i2})$ required to be fitted with the circle, a least square method is used to fit distances form all the points $P_i$ to points $T_i$, and minimization is carried out, $$d_i^2 = \min_{\varphi_i}[(x_{i1} - x(\varphi_i))^2 + (x_{i2} - y(\varphi_i))^2], \sum_{i=1}^{m} d_i^2 = \min,$$

further, in order to obtain the contribution of different pixel coordinates to the circle fitting, the minimization may be made as $$\sum_{i=1}^{m} w_i * d_i^2 = \min,$$

$w_i$ is a weight coefficient.

The embodiments described with reference to the drawings are exemplary and are intended to be illustrative of the invention and are not to be construed as limiting the invention. The examples should not be construed as limiting the invention, and any modifications based on the spirit of the invention are intended to be within the scope of the invention.

The invention claimed is:

1. A method for processing pupil tracking images, comprising the steps of:
   1) acquiring multiple eye images;
   2) processing each acquired eye image, and determining whether a pupil can be positioned in the acquired image; and
   3) determining that the pupil tracking is completed when the pupil can be positioned in multiple consecutive eye images of the multiple eye images;
   wherein in step 2), the processing method for each acquired eye image includes the steps of:
   step 1, searching bright spots formed by projection of illumination light on a pupil;
   step 2, performing Blob analysis on the bright spots to determine a potential pupil area;
   step 3, carrying out gray normalization on the potential pupil area and carrying out multi-scale binarization;
   step 4, finding a potential circular area through Blob analysis, and obtaining a gravity center and a rough radius of the circular area;
   step 5, taking the gravity center obtained in the step 4 as the center of a circle, adopting a 360-degree outward line drawing method to obtain gray level jump, and obtaining the maximum gray level jump of the left, right and lower parts of the pupil, namely the maximum jump being the boundaries of the left, right and lower parts of the pupil;
   step 6, obtaining a boundary and determining the reliability of the boundary by adopting a support vector machine (SVM) according to a gray value obtained by a line drawing method, the boundary being an upper edge area of the pupil; and step 7, according to the boundaries of the left, right, lower and upper parts of the pupil obtained in step 5 and step 6, the pupil is obtained by using a least square method to fit a circle.

2. The method for processing pupil tracking images according to claim 1, wherein in step 5, the relationship between the gray level on each drawn line and the distance is obtained.

3. The method for processing pupil tracking images according to claim 1, wherein in step 2, a pupil image obtained by eccentric photography optometry is examined, and whether the pupil moves or not is determined by judging a shape of the light spot.

4. The method for processing pupil tracking images according to claim 1, wherein in step 3, a multi-scale binarization threshold value is determined according to the gray mean value, the gray standard deviation, the gray minimum value and the gray maximum value of the pupil image, wherein the binarization threshold value=gray mean value-α*gray standard deviation, and the coefficient α is an empirical value.

5. The method for processing pupil tracking images according to claim 1, wherein in step 6, a boundary is obtained by using a support vector machine (SVM) through the gray value sequence obtained by the 360-degree outward line drawing method in step 5.

6. The method for processing pupil tracking images according to claim 1, wherein in step 5, the maximum jump of the gray level is obtained through a difference method.

7. The method for processing pupil tracking images according to claim 1, wherein in step 7, a parameter equation of the circle is established as follows:

$$x = z_1 + r\cos\varphi$$

$$y = z_2 + r\sin\varphi$$

wherein $(z_1, z_2)$ is the coordinate of the circle center, r is a radius of the circle, $\varphi$ is a parameter, and each point on the circle is $T_1 = (x(\varphi_i), y(\varphi_i))$, for an image pixel coordinate $P_i = (x_{i1}, x_{i2})$ required to be fitted with the circle, a least square method is used to fit distances form all the points $P_i$ to points $T_i$, and minimization is carried out, $$d_i^2 = \min_{\varphi_i}[(x_{i1} - x(\varphi_i))^2 + (x_{i2} - y(\varphi_i))^2], \sum_{i=1}^{m} d_i^2 = \min,$$

further, in order to obtain the contribution of different pixel coordinates to the circle fitting, the minimization may be made as $$\sum_{i=1}^{m} w_i * d_i^2 = \min,$$

$W_i$ is a weight coefficient.

8. The method for processing pupil tracking images according to claim 1, wherein in step 3), a number of multiple consecutive eye images of the multiple eye images is six consecutive eye images.

* * * * *